United States Patent
Elfring et al.

(10) Patent No.: US 9,491,835 B2
(45) Date of Patent: Nov. 8, 2016

(54) METHOD FOR IMPROVING THE ILLUMINATION OF AN ILLUMINATION REGION FROM AN ILLUMINATION DEVICE

(71) Applicants: Robert Elfring, Lübeck (DE); Frank Franz, Stockelsdorf (DE); Hanno Kretschmann, Hamburg (DE); Stefan Schlichting, Lübeck (DE)

(72) Inventors: Robert Elfring, Lübeck (DE); Frank Franz, Stockelsdorf (DE); Hanno Kretschmann, Hamburg (DE); Stefan Schlichting, Lübeck (DE)

(73) Assignee: DRÄGERWERK AG & CO. KGAA, Lübeck (DE)

( * ) Notice: Subject to any disclaimer, the term of this patent is extended or adjusted under 35 U.S.C. 154(b) by 0 days.

(21) Appl. No.: 14/902,130

(22) PCT Filed: Jun. 20, 2014

(86) PCT No.: PCT/EP2014/001688
§ 371 (c)(1),
(2) Date: Dec. 30, 2015

(87) PCT Pub. No.: WO2015/010757
PCT Pub. Date: Jan. 29, 2015

(65) Prior Publication Data
US 2016/0174336 A1    Jun. 16, 2016

(30) Foreign Application Priority Data
Jul. 23, 2013   (DE) .......................... 10 2013 012 231

(51) Int. Cl.
H05B 37/02      (2006.01)
F21V 23/04      (2006.01)
H05B 33/08      (2006.01)
F21W 131/205    (2006.01)

(52) U.S. Cl.
CPC .......... *H05B 37/0227* (2013.01); *A61B 90/30* (2016.02); *F21V 23/0471* (2013.01); *F21W 2131/205* (2013.01); *H05B 33/0815* (2013.01)

(58) Field of Classification Search
CPC .......... H05B 33/0845; H05B 33/0872; H05B 33/0869; H05B 33/08; H05B 33/0842
USPC ............ 315/158, 149, 150, 156, 159, 185 S, 315/209 R
See application file for complete search history.

(56) References Cited

U.S. PATENT DOCUMENTS 6,880,957 B2 *   4/2005   Walters ............... F21V 23/0442
                                                           250/205
2003/0185009 A1   10/2003  Walters (Continued)

FOREIGN PATENT DOCUMENTS

| EP | 1 568 937 A1 | 8/2005 |
| EP | 1741975 A2 | 1/2007 |
| WO | 2013/088312 A1 | 6/2013 |

*Primary Examiner* — Tuyet Vo
(74) *Attorney, Agent, or Firm* — McGlew and Tuttle, P.C.

(57) ABSTRACT

A method for improving the illumination of an illumination region (100), in particular of an operation region, from an illumination device (10), includes at least two light modules (20) and at least one sensor device (30) for detecting depth information. The method includes the steps of monitoring a monitored volume (110) between the light modules (20) and the illumination region (100), identifying the position and the geometry as object data of at least one object (200) within the monitored volume (110), comparing the identified object data with beam paths (S) from the light modules (20), and modifying the light intensity of at least one light module (20) on the basis of the comparison between the identified object data with beam paths (S) from the light modules (20).

20 Claims, 5 Drawing Sheets

(56) References Cited

U.S. PATENT DOCUMENTS

2010/0277073 A1* 11/2010 Van Endert ............ G06F 3/017 315/149

2010/0277080 A1* 11/2010 Waffenschmidt .. H05B 37/0245 315/152

2014/0339985 A1* 11/2014 Engelen ................ G06F 3/0421 315/151

* cited by examiner

METHOD FOR IMPROVING THE ILLUMINATION OF AN ILLUMINATION REGION FROM AN ILLUMINATION DEVICE

CROSS REFERENCE TO RELATED APPLICATIONS

This application is a U.S. National Phase Application of International Application PCT/EP2014/001688 filed Jun. 20, 2014 and claims the benefit of priority under 35 U.S.C. §119 of German Patent Application 10 2013 012 231.7 filed Jul. 23, 2013 the entire contents of which are incorporated herein by reference.

FIELD OF THE INVENTION

The present invention pertains to a method for improving the illumination of an illuminated area of an illuminating device, to a corresponding illuminating device as well as to the use of such an illuminating device for a lighting fixture of an operating room.

BACKGROUND OF THE INVENTION

It is known that illuminating devices are used, e.g., for lighting fixtures of operating rooms. The illuminating device has for this at least two light modules, which are capable of emitting light. This emitted light is used to make available the brightening of an illuminated area. This area is especially the operating area, so that the illumination of a wound during a surgical procedure can be guaranteed by such an illuminating device. It is decisive in this connection that a sufficient brightness level be reached within the illuminated area in order to make it possible to perceive especially differences in color as well as shadings within the illuminated area unambiguously and as specifically as possible.

The drawback of prior-art illuminating devices is that it is necessary to work within the illuminated area. This causes cast shadows to inherently occur within the illuminated area. If the illuminating device is, e.g., an operating lamp, the surgeon in charge must be positioned with his hands, his arms and partly even with his head between the illuminating device and the illuminated area. This causes these individual body parts to cast a shadow on the illuminated area. The illuminated area is usually a focusing starting from an illuminating device designed as a relatively broad device. If a body part of the surgeon is located between the illuminating device and the illuminated area, the illuminated area is essentially even darkened completely and the visibility conditions deteriorate. The prior-art solutions for thus avoiding shadow formation are aimed at providing especially broad illuminating devices. However, this leads to a great design effort, so that such illuminating devices are especially cost-intensive. Sufficient space may also be lacking at some sites of use for accommodating such especially large illuminating devices in the first place. Last but not least, the operability of such especially large illuminating devices has drawbacks.

SUMMARY OF THE INVENTION

An object of the present invention is to eliminate at least one of the above-described drawbacks. In particular, an object of the present invention is to provide an improved illumination situation for the illuminated area in a cost-effective and simple manner.

The above object is accomplished by a method according to the invention, and by an illuminating device according to the invention. Features and details that are described in connection with the method according to the present invention also apply, of course, in connection with the illuminating device according to the present invention as well as the operation of an illuminating devices and also vice versa in each case, so that reference is and can always mutually be made concerning the disclosure to the individual aspects of the present invention.

A method according to the present invention is used to improve the illumination of an illuminated area, especially of an operating area, of an illuminating device. This illuminating device has for this, especially in the form of a lighting fixture for an operating room, at least two light modules and at least one sensor device for detecting depth information. A method according to the present invention has the following steps:

monitoring a monitored volume between the light modules and the illuminated area,
  detecting the position and of the geometry as object data of at least one object within the monitored volume,
  comparing the detected object data with beam paths of the light modules, and
  modifying the light intensity of at least one light module on the basis of (as a function of) the comparison of the detected object data with beam paths of the light modules.

An illuminated area is defined especially as an area of the entire light field of the illuminating device. The entire light field and the illuminated area may, of course, also be designed such that they are congruent. It is also possible that individual areas or a plurality of areas of the light field are designed as illuminated area.

The light intensity of at least one light module is adapted by a method according to the present invention to detect objects within the monitored volume. The monitored volume is defined here as a volume which extends at least partly between the illuminating device and the illuminated area. In particular, this monitored volume covers the illuminated volume at least partly, i.e., the sum of all beam paths originating from the light modules, which fall on the illuminated area. It is advantageous if the overlap between this illuminated volume and the monitored volume is made as large as possible. In particular, the area starting from the illuminated area for the illuminated volume is overlapped essentially completely by the monitored volume. However, it may happen in the direction of the illuminating device that a detection distance is maintained, so that there does not have to be an overlap between the monitored volume and the illuminated volume immediately following the illuminated area. The depth information is defined especially as a three-dimensional space information.

It becomes possible due to the method according to the present invention to carry out a monitoring of potential objects in terms of position and geometry within the above-described monitored volume. If such an object is detected, not only the presence in general, but also the position and, at least from the view of the sensor device, the geometry are also detected as object data of this object. These object data can now be compared with the individual beam paths of the light modules, i.e., basically with the illuminated volume already described. However, the object and the object data are compared basically not only with the illuminated volume, but also with the individual beam paths of individual light modules, so that a correlation of covered and free beam paths can be established between light modules and the object data of the object. In other words, a correlation can be established on which beam paths of which light modules are covered by the detected object. By implication, it is possible to define beam paths that, unaffected by the detected object, can reach the illuminated area from the light module in question. Thus, affected beam paths can be distinguished from unaffected beam paths concerning an influence, i.e., a shadowing caused by the object by the detection of the object data and the comparison thereof with the beam paths of the light modules. The light modules can thus be divided essentially into three different shadowing situations. If all beam paths of a light module are unaffected by the object and consequently no shadowing occurs within these beam paths, the light module is a unshadowed light module. Contrary to this, if all beam paths of this light module are affected by the object, the light module is a fully shadowed light module. If only some of the beam paths of a light module are affected by the object, e.g., in case of a light module with a plurality of light sources, this light module can be defined as a partly shadowed light module.

The different definition of the individual light modules, which was explained in the preceding paragraph, is taken into account in the above-mentioned modification of the light intensity of at least one light module. Thus, an object will lead, in principle, to shadowing and hence to a reduction of the light intensity in the illuminated area. This reduction of the light intensity is, as was explained, undesirable, so that a compensation shall be effected. This compensation takes place by different light modules being operated with a higher light intensity or with a higher light emission output. In other words, a compensation is effected in the illuminated area, so that shadowed beam paths can be compensated by intensified beam paths of unaffected light modules. Based on the penetration of an object into the monitored volume, the weighting of the light intensity is shifted between the individual light modules. Unshadowed light modules thus assume the light emission of shadowed or partly shadowed light modules, so that ultimately a constant or essentially constant light intensity can be made available in the illuminated area.

The definition of a modification of the light intensity of at least one light module also includes the affecting of the partly shadowed or fully shadowed light modules. Thus, the light emission of fully shadowed light modules can be reduced or even switched off completely. Since the beam paths are fully affected by the object and they correspondingly cannot reach the illuminated area for illuminating same any longer, they also do not make any contribution to the desired overall intensity in the illuminated area. To save energy and also to achieve an improvement concerning heat emission, the light emission of such fully shadowed light modules can be correspondingly reduced or even switched off completely.

Two basic modes of operation can be distinguished in case of partly shadowed light modules. Thus, a distinction shall be made on what overall intensity is desired in the illuminated area and whether this can be reached by the remaining unshadowed light modules by increasing the light intensity of these modules. If this cannot be done, an additional light emission is not necessary any longer, so that the light intensity of the partly shadowed light modules can remain the same or even be reduced. If, however, the increased light intensity of the unshadowed light modules is not sufficient, e.g., due to shadowing of a large area by an object, to compensate the shadowing or to essentially compensate the shadowing, partly shadowed light modules can also be operated with an increased light intensity in order to entail a compensation or a partial compensation of the shadowing in the illuminated area with the unshadowed beam paths. Even though this entails a needless increase in the light intensity in this way for the shadowed beam paths, the unshadowed beam paths can contribute to the compensation in order to bring about the best possible compensation of the shadowing concerning the overall illumination intensity in the illuminated area even in case of shadowing of a large area.

A sensor device is, in the sense of the present invention, especially a camera device, preferably a so-called 3D camera. It is designed as (configured as) a depth information system (so-called DIS) and yields depth information, on the basis of which the position and the geometry can be detected as object data of an object within the monitored volume. A sensor device may have, of course, one or even more sensor means. In particular, individual depth information images are superimposed in order to make it possible to make the object data described available especially accurately.

A calibration step may, of course, be performed in advance for a method according to the present invention in order to make it possible to assign the individual beam paths to the light modules in a control unit. Calibration of the sensor device in respect to the detected depth information and a correlation with the object data may also be performed as a separate step at the beginning of the method according to the present invention.

Especially the contour in the direction of radiation, i.e., along the beam paths for the object, is decisive concerning the detection of the position and the geometry of the object. What is therefore preferred is not the three-dimensional extension of the object, but rather the projection area of the object in the direction of the beam path. In other words, what is detected is not the three-dimensional extension of the object but the shadowing effect of the object with correlation with the existing beam paths of the light modules. A different geometry may also be able to be detected as object data for each object relatively for differently oriented light modules. This depends quasi on the correlation of the sensor device and the comparison of the particular light module.

The rate of modification of the light intensity, i.e., especially the rate of compensation of the shadowing, will preferably be less than one second. A rate of compensation, i.e., a rate of modification in the range of less than about 0.2 sec is preferred. In particular, a comparison is performed concerning the illumination intensity in the illuminated area for a required minimum intensity. However, it may also be advantageous if it is ensured that a maximum intensity is not exceeded by a comparison. The operational reliability is further increased in this way. Thus, an intensity monitoring device, which is capable of determining the real actual situation concerning the illumination quality in the illuminated area, may additionally be arranged.

In addition to focusing the light, collimation or near-collimation, especially with small divergence angles, is also possible for illuminating the illuminated area with the light modules. Further advantages of a method according to the present invention are the reduction of unnecessary release of heat from the illuminating device, a reduction of the space requirement for the illuminating device and avoidance of undesired light fluctuations.

It may be advantageous if the method steps in a method according to the present invention, especially the detection of the object data and the comparison with the beam paths of the light modules are performed repeatedly in a loop. The monitoring for shadowing objects is thus performed continuously or semicontinuously or quasi-continuously by a method according to the present invention when a lighting device according to the present invention is used. The loop is quasi an iteration of the method, so that monitoring for potential shadowing by objects is carried out continuously. If an object is detected, an averaging of the object data may also be performed based on the repetition of the loop in order to make available an improved detection and reduced-error detection of object data in the method over a plurality of detection rounds. The loop is also monitored with respect to the performance over time in order to avoid a compensation, e.g., in case of especially short-term shadowing. Rapid deviations for the individual light intensity settings of the light modules are preferably avoided in this way. Undesired and erratic light situations, e.g., light flashes and rapid consecutive changes between illumination situations of the illuminated area, can be avoided in this way especially effectively. Provisions are thus preferably made for carrying out the method continuously for making the functionality according to the present invention continuously available. An averaging of the values determined over the iterations may thus take place as well.

It may likewise be advantageous if the steps of modifying the light intensity of at least one light module take place in a damped manner and especially damped over time in the method according to the present invention. A damped manner of modification over time means that abrupt modifications in the light intensity of the individual light modules are avoided. In particular, rapid jumps in regulation or changes in the regulation are avoided in this way. Light flashes during short-term shadowing can be prevented in this way from occurring. In other words, this is a forced control inertia used to avoid improved acceptance by the user and especially to avoid rapid changes in brightness, which would cause the user to become distracted while performing his work proper. The damping is preferably essentially a damping of the step of reducing the light intensity, i.e., the darkening of light modules. The compensation by intensifying the light intensity of individual light modules preferably takes place without damping and correspondingly as rapidly as possible. Undamped regulation preferably likewise takes place when a shadow caused by the object is eliminated in order to avoid an excessively bright illumination as much as possible. It is also possible to perform an averaging of the object detection over a plurality of performances of the present invention. This avoids a modification of the light intensity in case of an only brief shadowing.

It may likewise be advantageous if a local shadowing of the illuminated areas is assigned to a light module in a method according to the present invention by the step of comparison for each light module. Shadowing situations can thus be assigned to individual light modules due to the above-described correlation between beam paths and light modules. As was likewise explained above, light modules can be distinguished as fully shadowed light modules, unshadowed light modules and partly shadowed light modules. Consequently, an explicit correlation develops between the shadowing by the object and the corresponding light module. An improved basis is thus made available for the subsequent control of the compensation, as it was already explained in detail.

It may, furthermore, be advantageous in a method according to the explanation given in the above paragraph if the light intensity of at least one light module is increased and/or the light intensity of the light module with the assigned shadowing is reduced. Distinction is to be made here, in particular, between fully shadowed light modules and unshadowed light modules. The light intensity generated by unshadowed light modules is increased, in particular, in order to achieve compensation of shadowing. The light intensity produced by fully shadowed light modules is reduced in order to avoid energy consumption and needless generation of heat. Both directions are conceivable in case of partly shadowed light modules in order to achieve, on the one hand, the above-described compensation even in case of large-area shadows by increasing the light intensity in case of partly shadowed light modules. If the increased light intensity of the unshadowed light modules is sufficient for compensating a shadow generated by an object, the partly shadowed light modules can be operated with unchanged or even reduced light intensity.

It is likewise advantageous if the detection of the object data of at least one object within the monitored volume is carried out in a method according to the present invention with a monitoring angle of about ≥45°. The monitoring angle is defined here especially as an essentially conical or truncated pyramid-shaped monitoring volume, which extends starting from an apex of the cone at the sensor device. The monitoring angle is thus the opening angle of the cone of this monitored volume. The larger this monitoring angle, the higher, i.e., the closer to the illuminating device can be the site be at which the monitoring takes place. The monitoring distance beginning from which the monitoring of the monitored volume can take place is consequently reduced. The monitoring is thus improved due to an enlargement of the monitored volume, so that the improvement of illumination according to the present invention in the illuminated area can be achieved with greater reliability. Even monitoring angles as large as about ≥60° are preferred. However, other angles, also angles up to about 120° or greater, are also conceivable in the sense of the present invention.

It may likewise be advantageous if the detection of the object data of at least one object within the monitored volume is carried out in a method according to the present invention with a detection distance in range of between about 10 cm and about 150 cm. The first 10 cm of the distance between the illuminating device and the monitoring volume are essentially irrelevant, because an object is very unlikely to be arranged there. In particular, a user of the illuminating device will avoid positioning his body parts there, because he would otherwise possibly have to eliminate sterility problems. A detection distance starting from about 10 cm starting from the illuminating device to about 150 cm is decisive. Usual distances between the illuminating device and the illuminated area are in the range of about 100 cm. Reduction of the detection distance to the described values leads especially to a reduction of the cost of the sensor system, e.g., of the sensor device.

It is likewise advantageous if a calibration step is performed in a method according to the present invention for the detection of the working distance between the illuminating device and the illuminated area. The detection of the working distance, i.e., of the distance between the illuminating device and the illuminated area, is performed during the calibration. This calibration step is preferably carried out rather frequently and can make available from time to time an interim calibration of the illuminating device, e.g., in case of fixed distances. In other words, there is a resetting to zero for the start of the method according to the present invention. The comparison of the detection of the objects is performed with the calibrated working distance, so that the described comparisons can be carried out for the beam paths of the light modules. It is also possible that transformation matrices, which can make a calculable distinction between different coordinate systems of the light modules, of the sensor device and of the real coordinate system, are provided by a calibration. This takes place, in particular, in case of the combination with an automated adjustment of the illuminating device. It is possible to use the sensor device for the calibration. The calibration may also take place iteratively during the illumination and thus it can be renewed at regular intervals.

It may likewise be advantageous if the steps of detecting the working distance between the illuminating device and the illuminated area as well as the comparison of the detected working distance with a predefined value for the working distance are additionally carried out in a method according to the present invention. In addition to the basic functionality of compensating shadowings by objects according to the present invention, a modification of illumination due to an erroneous working distance is achieved in this way. An illuminating device has a focusing of the beam path, so that there is an ideal working distance for ideal focusing with increased intensity. If the working distance changes away from this ideal working distance, the manner of focusing and consequently the light intensity in the illuminated area will be reduced as well. In other words, a reduction of the illumination is likewise achieved in the illuminated area by an erroneous working distance, without shadowing objects being present. The method according to the present invention is consequently also used for such a reduction of the light intensity for compensation, and can make available the desired illumination situation in the illuminated area by increasing the light intensity of all light modules in case of an incorrect or erroneous working distance.

The present invention also pertains to an illuminating device for illuminating an illuminated area, having at least two light modules with at least one illuminant each and with at least one sensor device for detecting depth information. Further, a control unit is provided, especially for carrying out a method according to the present invention. An illuminating device according to the present invention correspondingly brings with it the same advantages as those explained in detail with reference to a method according to the present invention. The light modules are equipped with light sources, for example, in the form of LEDs. Fast switching can thus be achieved with a compact design of the light modules. The cost of the light modules of this design is low as well.

It is advantageous in an illuminating device according to the present invention if the control unit is designed, furthermore, for modifying the light intensity of at least one of the light modules on the basis of (as a function of) the detected object data with beam paths of the light modules. In particular, the corresponding method steps of a method according to the present invention are carried out, as a result of which the corresponding advantages described can be achieved.

It may likewise be advantageous if at least two sensor means of the sensor device, which are arranged at spaced locations from one another, are provided in an illuminating device according to the present invention. At least one sensor means may be now be arranged in the center of the illuminating device. A completely non-central arrangement of different sensor means may also bring advantages with it for an improved detection of the desired depth information.

Further, the present invention pertains to the use of an illuminating device according to the present invention or of a method according to the present invention for a lighting fixture of an operating room. The illumination in the illuminated area, i.e., in the operating area, is of crucial significance for the quality with which the work, i.e., the surgery, is performed, especially in case of lighting fixtures for operating rooms. A method according to the present invention and a functionality according to the present invention of an illuminating device correspondingly have especially great advantages precisely in case of such intended uses.

Further advantages, features and details of the present invention appear from the following description, in which exemplary embodiments of the present invention are specifically described with reference to the drawings. The features mentioned in the claims and in the description may be essential for the present invention individually or in any combination.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF THE PREFERRED EMBODIMENTS

Figure 1:
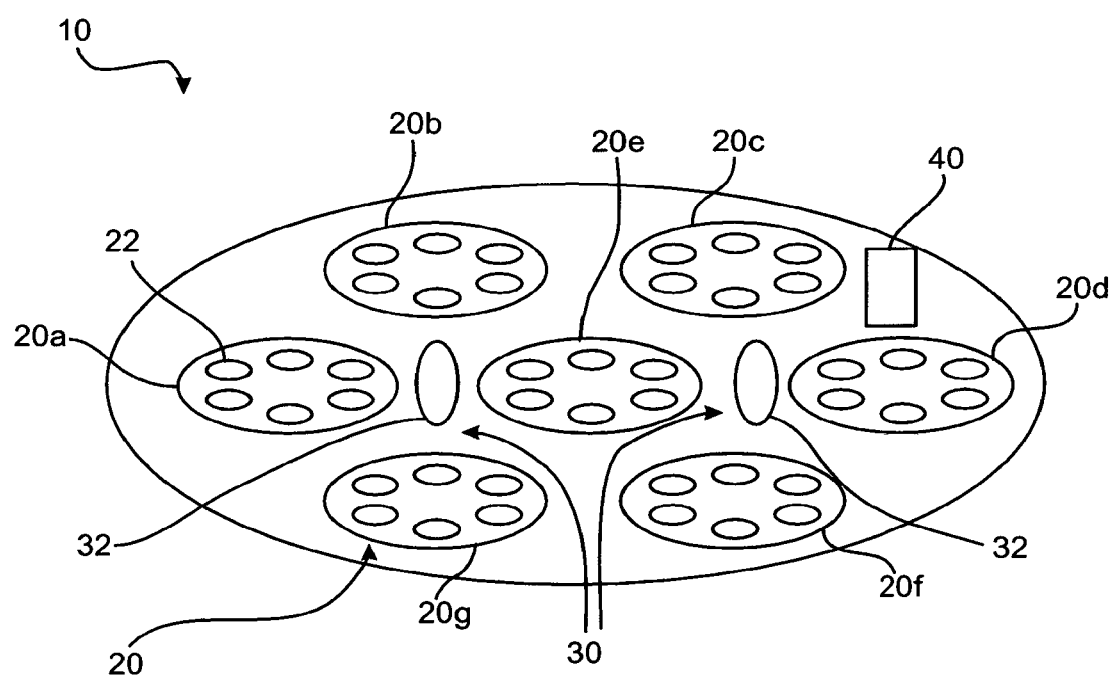
FIG. 1 is a schematic view of a first embodiment of an illuminating device according to the present invention.
Figure 2:
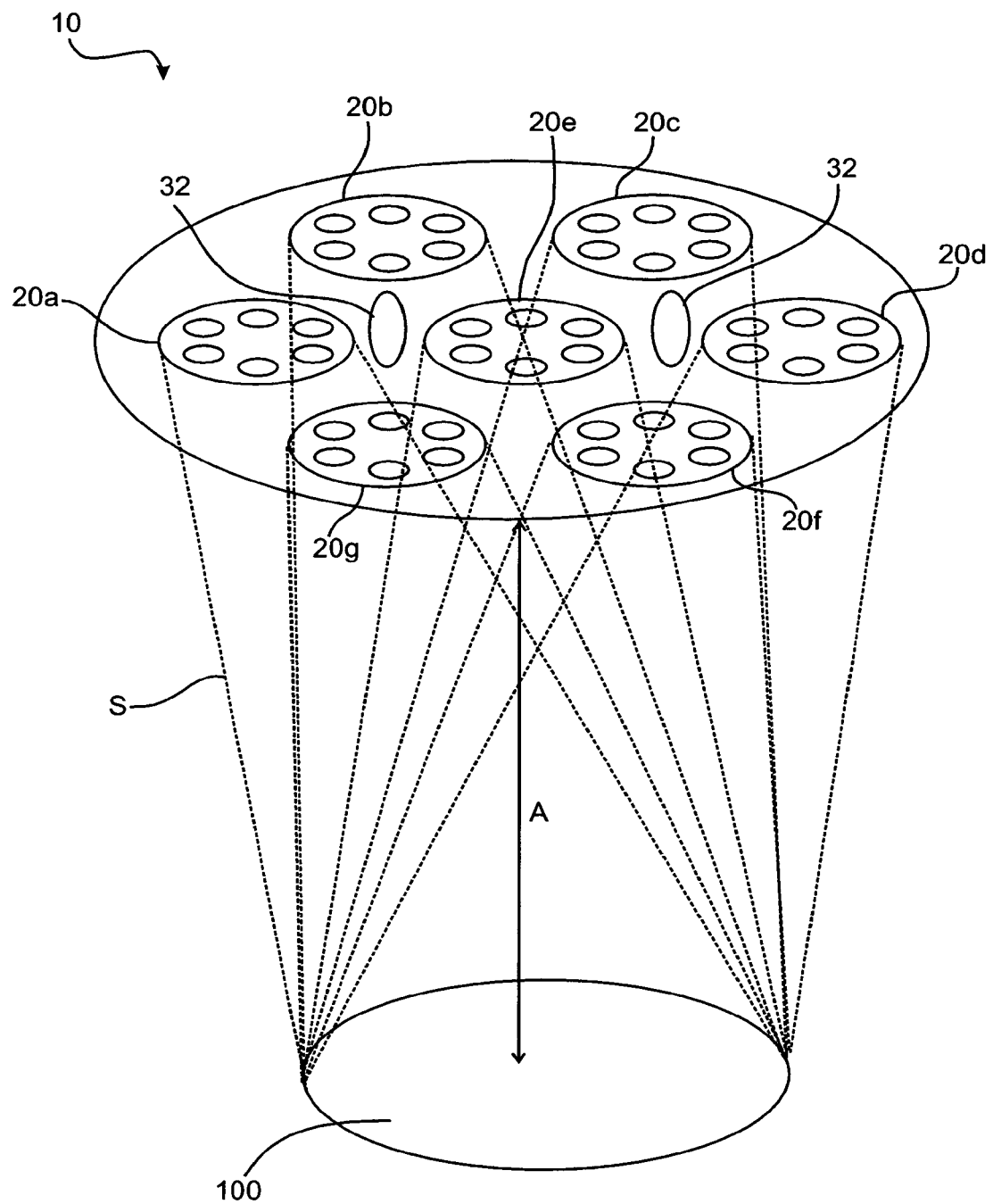
FIG. 2 is a schematic view of the embodiment according to FIG. 1 with the beam paths shown.
Figure 3:
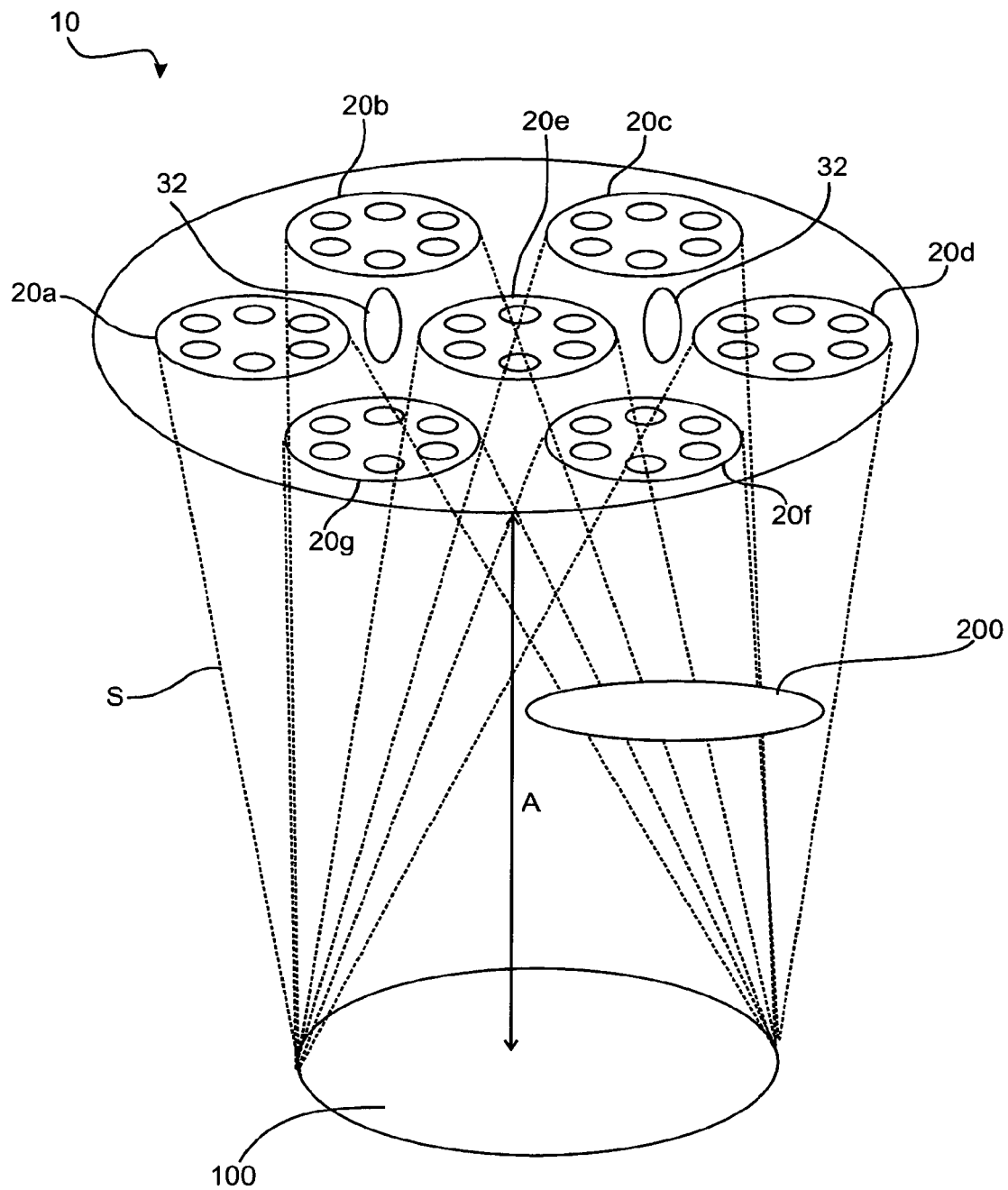
FIG. 3 is a schematic view showing the embodiments according to FIGS. 1 and 2 with an introduced object.

FIGS. 1 through 3 show a first embodiment of an illuminating device 10 according to the present invention. This has a plurality of light modules 20, namely, the light modules 20a through 20g. Moreover, two sensor means 32 are provided as a sensor device 30. A control unit 40 is also formed, which is in signal-communicating contact with the sensor device 30, The sensor means 32 are designed for detecting depth information.

FIG. 2 shows a possible arrangement of an illuminating device 10, The individual light modules 20 (20a through 20g) produce an illuminated area 100, which is arranged at a working distance A from the illuminating device 10. Some beam paths S for the light modules 20 are schematically indicated. Thus, all beam paths overlap within the illuminated areas 100 and generate there as a sum the desired overall intensity in this illuminated area 100. It is, however, also possible within the framework of the present invention that the beam paths overlap only partly or do not overlap at all.

FIG. 3 shows the situation according to FIG. 2 after the penetration of an object 200 into the corresponding monitored volume 110, which will be shown later, e.g., in FIG. 4. The detection of the object 200 takes place in respect to object data relative to the geometry and position of the object 200. The detection is effected by the sensor means 32 of the sensor device 30. It will be explained below on the basis of FIGS. 4 and 5 how a method according to the present invention can be carried out.

Figure 4:
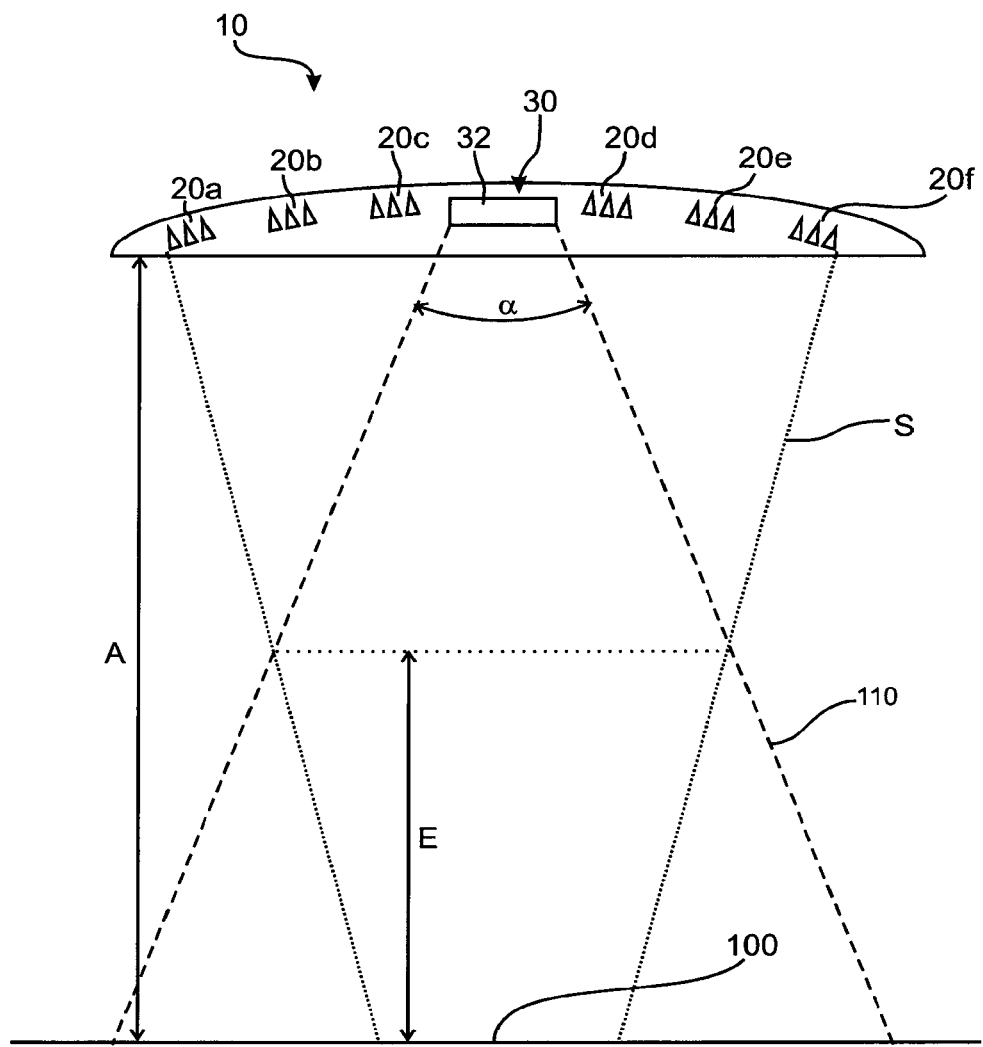
FIG. 4 is a schematic view of another embodiment of an illuminating device according to the present invention.
Figure 5:
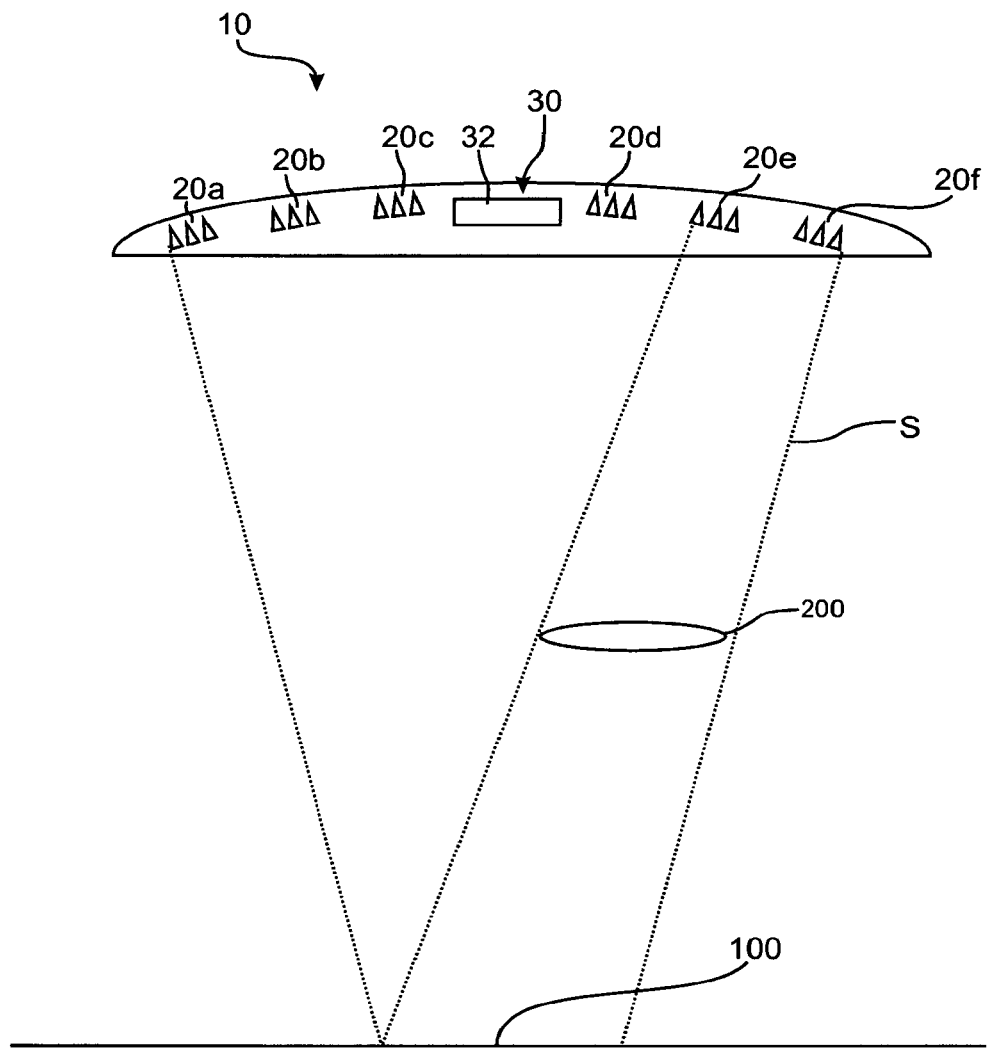
FIG. 5 is a schematic view showing the embodiment according to FIG. 4 with an introduced object.

FIGS. 4 and 5 also show an embodiment of an illuminating device 10. Light modules 20a through 20f, which have three light sources each, can be distinguished here. The working distance A can again be clearly seen in FIG. 4. The sensor means 32 of the sensor device 30 also has a monitoring angle α, which leads to an essentially truncated cone-shaped form of a monitored volume 110. The outermost beam paths S from the outermost light modules 20 define here the light cone, which falls on the illuminated area 100 in a focusing manner. The intersection of the light cone and of the monitored volume 110 forms the boundary for the detection distance E, which is especially relevant for the detection of objects 200.

If an object 200 enters the monitored volume 110, as this is shown in FIG. 5, it is detected by the sensor device 30 in respect to its object data, i.e., in respect to the position and size. As is shown, e.g., in FIG. 5, a comparison is subsequently made with the beam paths S. It is seen in this comparison that the two light modules 20e and 20f are fully shadowed in the arrangement according to FIG. 5. This means that the beam paths S starting from these two light modules 20e and 20f are no longer able to make their contribution to the illumination intensity available in the illuminated area 100. The beam paths of the light modules 20a through 20c are not shadowed, so that an increase in the light intensity of these three light modules 20 can bring about a compensation of the shadowing, i.e., of the reduced illumination with the overall intensity in the illuminated area 100. The last light module 20d represents a partly shadowed state. Thus, if the increase in the light intensity of the light modules 20a through 20c is not sufficient, the light intensity of the light module 20d may be increased as well. The unshadowed part of the beam paths thus likewise contributes to the described compensation. However, if the increase in the intensity of the light modules 20a through 20c is already sufficient for the desired compensation of the illumination in the illuminated area 100, it is also possible, e.g., to reduce the intensity of the partly shadowed light module 20d.

The light intensity of the light modules 20e and 20f, which are fully shadowed by the object 200, is preferably reduced or these light modules are even switched off completely. Needless energy consumption and undesired heating of the object 200 are thus avoided or reduced.

The above explanation of the embodiments describes the present invention exclusively within the framework of examples. Individual features of the embodiments, if technically meaningful, may, of course, be freely combined with one another without going beyond the scope of the present invention.

While specific embodiments of the invention have been shown and described in detail to illustrate the application of the principles of the invention, it will be understood that the invention may be embodied otherwise without departing from such principles.

The invention claimed is:

1. A method for improving the illumination of an illuminated area of an operating area, the method comprising the steps of:
   providing an illuminating device with at least two light modules and with at least one sensor device for detecting depth information;
   monitoring a monitored volume between the light modules and the illuminated area;
   detecting a position and geometry as object data of at least one object within the monitored volume;
   comparing the detected object data with beam paths of the light modules; and
   modifying a light intensity of at least one light module on the basis of the comparison of the detected object data with beam paths of the light modules.

2. A method in accordance with claim 1, wherein the method steps, especially the detection of the object data and the comparison with the beam paths of the light modules, are carried out repeatedly in a loop.

3. A method in accordance with claim 1, wherein the step of modifying the light intensity of at least one light module is carried out in a damped manner time.

4. A method in accordance with claim 1, wherein the detection of the object data of at least one object within the monitored volume is carried out with a monitoring angle greater than or equal to about 45°.

5. A method in accordance with claim 1, wherein the detection of the object data of at least one object within the monitored volume is carried out with a detection distance in the range of about 10 cm to about 150 cm.

6. A method in accordance with claim 1, further comprising a calibration step carried out as a first step for detecting a working distance between the illuminating device and the illuminated area.

7. A method in accordance with claim 1, further comprising the steps of detecting a working distance between the illuminating device and the illuminated area and comparing the detected working distance with a predefined value for the working distance.

8. A method in accordance with claim 1, wherein a local shadowing of the illuminated area is assigned to a light module by the step of comparison for each light module.

9. A method in accordance with claim 8, wherein at least one of the light intensity of at least one light module is increased and the light intensity of the light module with the assigned shadowing is reduced.

10. An illuminating device for illuminating an illuminated area, the illuminating device comprising:
    at least two light modules, each of the light modules comprising at least one illuminant;
    at least one sensor device for detecting depth information; and
    a control unit configured to:
    monitor a monitored volume between the light modules and the illuminated area;
    detect a position and geometry of at least one object within the monitored volume to generate object data corresponding to the detected position;
    compare the detected object data with beam paths of the light modules; and
    modify a light intensity of at least one of the light modules as a function of the comparison of the detected object data with beam paths of the light modules.

11. An illuminating device in accordance with claim 10, wherein the control unit is, configured for modifying the light intensity of at least one of the light modules as a function of detected object data in a comparison with beam paths of the light modules.

12. An illuminating device in accordance with claim 10, wherein the sensor device comprises two sensors arranged at spaced locations from one another.

13. An illuminating device in accordance with claim 10, wherein the detection of the object data and the comparison with the beam paths of the light modules are carried out by the control unit repeatedly in a loop.

14. An illuminating device in accordance with claim 10, wherein the modifying the light intensity of at least one light module is carried out with damping manner over time.

15. An illuminating device in accordance with claim 10, wherein the detection of the object data of at least one object within the monitored volume is carried out with a monitoring angle greater than or equal to about 45°.

16. An illuminating device in accordance with claim 10, wherein the detection of the object data of at least one object within the monitored volume is carried out with a detection distance in the range of about 10 cm to about 150 cm.

17. An illuminating device in accordance with claim 10 wherein the control unit is further configured for a calibration step as a first step for detecting a working distance between the illuminating device and the illuminated area.

18. An illuminating device in accordance with claim 10, wherein the control unit is further configured for detecting a working distance between the illuminating device and comparing the illuminated area and comparing the detected working distance with a predefined value for the working distance.

19. An illuminating device in accordance with claim 10, wherein a local shadowing of the illuminated area is assigned to a light module for the comparison for each light module.

20. An illuminating device in accordance with claim 19, wherein the control unit modifies the light intensity by at least one of increasing the light intensity of at least one light module and reducing the light intensity of the light module with the assigned shadowing.

* * * * *